United States Patent
Breuer et al.

(10) Patent No.: US 10,179,923 B2
(45) Date of Patent: Jan. 15, 2019

(54) METHOD FOR BIOCATALYTICALLY CYCLIZING GERANYLLINALOOL AND CYCLIZATION PRODUCTS THEREBY OBTAINED

(71) Applicant: BASF SE, Ludwigshafen (DE)

(72) Inventors: Michael Breuer, Darmstadt (DE); Ralf Pelzer, Fürstenberg (DE)

(73) Assignee: BASF SE, Ludwigshafen am Rhein (DE)

( * ) Notice: Subject to any disclaimer, the term of this patent is extended or adjusted under 35 U.S.C. 154(b) by 0 days.

(21) Appl. No.: 15/514,706

(22) PCT Filed: Sep. 28, 2015

(86) PCT No.: PCT/EP2015/072262
§ 371 (c)(1),
(2) Date: Mar. 27, 2017

(87) PCT Pub. No.: WO2016/050690
PCT Pub. Date: Apr. 7, 2016

(65) Prior Publication Data
US 2017/0233780 A1 Aug. 17, 2017

(30) Foreign Application Priority Data
Sep. 29, 2014 (EP) .................................. 14186830

(51) Int. Cl.
| | |
|---|---|
| *C12P 7/00* | (2006.01) |
| *C12P 5/00* | (2006.01) |
| *C12N 9/90* | (2006.01) |
| *C12N 9/88* | (2006.01) |
| *C12N 15/61* | (2006.01) |
| *C12P 17/06* | (2006.01) |
| *C07D 311/92* | (2006.01) |

(52) U.S. Cl.
CPC ............ *C12P 17/06* (2013.01); *C07D 311/92* (2013.01); *C12N 9/90* (2013.01); *C12Y 504/99017* (2013.01)

(58) Field of Classification Search
CPC ........... C12P 7/06; C12N 9/90; C12N 9/1085; C12Y 504/99017
USPC .......... 435/117, 125, 193, 233, 320.1, 254.2, 435/252.33
See application file for complete search history.

(56) References Cited

U.S. PATENT DOCUMENTS

| | | |
|---|---|---|
| 6,596,520 B1 | 7/2003 | Friedrich et al. |
| 8,759,043 B2 | 6/2014 | Breuer et al. |

FOREIGN PATENT DOCUMENTS

| | | |
|---|---|---|
| DE | 10019377 A1 | 10/2001 |
| EP | 1069183 A2 | 1/2001 |
| EP | 1149849 A1 | 10/2001 |
| WO | WO-2010/139719 A2 | 12/2010 |
| WO | WO-2012/066059 A2 | 5/2012 |

OTHER PUBLICATIONS

International Preliminary Report on Patentability for International Application No. PCT/EP2015/072262 dated Dec. 7, 2016 with English Translation Thereof Attached.
International Search Report for PCT/EP2015/072262 dated Nov. 11, 2015.
Written Opinion of the International Searching Authority for PCT/EP2015/072262 dated Nov. 11, 2015.
Daum, M., et al., "Genes and enzymes involved in bacterial isoprenoid biosysnthesis", Current Opinion in Chemical Biology, 2009, vol. 13, No. 180-188.
Günnewich, N., et al., "A diterpene synthase from the clary sage *Salvia sclarea* catalyzes the cyclization of geranylgeranyl diphosphate to (8R)-hydroxy-copalyl diphosphate", Phytochemistry, 2013, vol. 91, pp. 93-99.
Kato, T., et al., "Brominative Cyclisation of Nerolidol and Geranyllinalool", J.C.S. Chem Comm., 1980, vol. 23, pp. 1106-1108.
"Nomenclature Committee of the International Union of Biochemistry and Molecular Biology (NC-IUBMB)", Eur. J. Biochem., 1999, vol. 264, pp. 610-650.
Seo, J-S., et al., "The genome sequence of the ethanologenic bacterium *Zymomonas mobilis* ZM4", Nature Biotechnology, 2005, vol. 23, No. 1, pp. 63-68.
Siedenburg, G., et al., "Squalene-Hopene Cyclases", Applied and Environmental Microbiology, 2011, vol. 77, No. 12, pp. 3905-3915.

*Primary Examiner* — Robert B Mondesi
*Assistant Examiner* — Mohammad Y Meah
(74) *Attorney, Agent, or Firm* — Drinker Biddle & Reath LLP

(57) ABSTRACT

The present invention relates to a novel process for cyclizing geranyllinalool using the squalene-hopene cyclase from *Zymomonas mobilis* (Zm-SHC) or a cyclase with at least 80% sequence identity to the Zm-SHC, and cyclization products obtained in this process.

16 Claims, No Drawings

Specification includes a Sequence Listing.

METHOD FOR BIOCATALYTICALLY CYCLIZING GERANYLLINALOOL AND CYCLIZATION PRODUCTS THEREBY OBTAINED

RELATED APPLICATIONS

This application is a national stage application (under 35 U.S.C. § 371) of PCT/EP2015/072262, filed Sep. 28, 2015, which claims benefit of European Application No. 14186830.7, filed Sep. 29, 2014.

SUBMISSION OF SEQUENCE LISTING

The Sequence Listing associated with this application is filed in electronic format via EFS-Web and hereby incorporated by reference into the specification in its entirety. The name of the text file containing the Sequence Listing is Sequence_Listing_074012_0364. The size of the text file is 17 KB, and the text file was created on Mar. 27, 2017.

The present invention relates to a novel process for cyclizing geranyllinalool using the squalene-hopene cyclase from *Zymomonas mobilis* (Zm-SHC) or a cyclase with at least 80% sequence identity to the Zm-SHC, and cyclization products obtained in this process.

BACKGROUND OF THE INVENTION

The biosynthesis of a large number of monoterpenes in the corresponding production organisms has already been elucidated. Frequently, linear precursor molecules are cyclized by highly-specific biocatalysts. The precursors are, as a rule, esters of linear terpene alcohols and diphosphoric acid. A typical example of such a precursor is geranyl pyrophosphate. The pyrophosphate group is enzymatically eliminated from the molecule and subsequently hydrolyzed to give two phosphate ions. This gives rise on the other side to a carbo cation, which is now capable of undergoing further intramolecular reactions and recombines to give a cyclic monoterpene, for example with elimination of a proton (Curr. Opin. Chem. Biol. 2009, 13:180-188).

As, is known, non-activated triterpenes such as squalene or oxidosqualene are reacted in vivo by squalene-hopene cyclases (SHC) to give the corresponding cyclic compounds (Siedenburg, G. and Jendrossek, D., Applied and Environmental Microbiology, 2011, 77, (12), 3905).

The activity of certain squalene-hopene cyclases (SHC) is not limited to triterpenes. The international application PCT/EP2011/070304 (WO 2012066059 A2), the disclosure of which is herein expressly incorporated by reference in its entirety, describes squalene-hopene cyclase mutants which catalyze the cyclization of a citronellal isomer to an isopulegol isomer.

The international application PCT/EP2010/057696 (WO 2010139719 A2), the disclosure of which is herein expressly incorporated by reference in its entirety, proposes squalene-hopene cyclases as biocatalysts for the cyclization of homofarnesol to ambroxan.

The gene and protein sequences of the squalene-hopene cyclase from the bacterium *Zymomonas mobilis* (Zm-SHC) are known (Genpept Accession No AAV90172 2004 and Nat Biotechnol 2005, 23:63-68, cf. SEQ ID No. 1 and 2).

Object of the present invention was to provide a process for the cyclization of geranyllinalool.

SUMMARY OF THE INVENTION

The above problem was solved by a process for the biocatalytic cyclization of a compound of the formula (I)

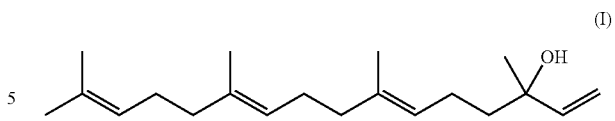

in the presence of a cyclase which has an amino acid sequence as shown in SEQ ID No. 2 or which has at least 80% sequence identity to SEQ ID No. 2.

Preferably, the compound of the formula (I) is reacted in the process according to the invention to give at least one compound of the formula (II)

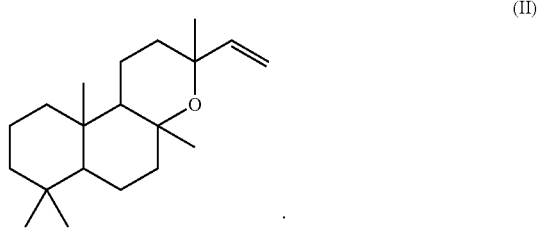 [SMILES: C=CC1(C)CCC2C(C)(CCC3C(C)(C)CCCC32C)O1]

The invention also relates to a compound of the formula (II).

DETAILED DESCRIPTION OF THE INVENTION

A. General Definitions

For the purposes of the present invention, "cyclases" are generally enzymes or enzyme mutants which display in particular the activity of a geranyllinalool cyclase. The activity of a geranyllinalool cyclase means an enzymatic activity for the isomerization of geranyllinalool (I) with the formation of at least one 5- or 6-membered ring, in particular a chromene-like, and especially a benzochromene-like, cyclized structure. Suitable enzymes with the activity of a geranyllinalool cyclase are intramolecular transferases from the subclass of the isomerases; that is to say proteins with the EC number EC 5.4 (enzyme code as per Eur. J. Biochem. 1999, 264, 610-650). In particular, they take the form of representatives of EC 5.4.99.17. Suitable enzymes with the activity of a geranyllinalool cyclase are, in particular, those cyclases which also bring about the cyclization of homofarnesol to ambroxan, of a citronellal isomer to an isopulegol isomer or of squalene to hopene (hence sometimes also designated "SHC" squalene-hopene cyclase) and which are described in detail in the international applications PCT/EP2010/057696 and PCT/EP2011/070304, to which reference is expressly made here.

Owing to the reversibility of enzymatic reactions, the present invention relates to the enzymatic reactions described herein in both directions of reaction.

"Functional mutants" of a "cyclase" comprise the "functional equivalents" of such enzymes, which are defined hereinbelow.

The term "biocatalytic process" relates to any "process for the biocatalytic cyclization of a compound of the formula (I)", i.e. process in the presence of crude, purified, dissolved, dispersed or immobilized enzyme, or in the presence of cyclase-displaying cells of a microorganism which display or express the activity of a geranyllinalool cyclase. Biocatalytic processes thus comprise both enzymatic and microbial processes and also fermentative processes.

The term "stereospecific" means that one of several possible stereoisomers of a compound with at least one asymmetry center, which compound is produced in accordance with the invention, is produced by the action of an inventive enzyme in high "enantiomeric excess" or high "enantiomeric purity", for example at least 90% ee, in particular at least 95% ee or at least 98% ee or at least 99% ee. The ee % value is calculated by the following formula:

ee %=[$X_A$-$X_B$]/[$X_A$+$X_B$]*100, in which $X_A$ and $X_B$ stand for the molar fraction of the enantiomers A and B, respectively.

"First sphere residues" and "second sphere residues" are amino acid residues which, based on structural analyses of the protein, are assigned a special proximity to the reactive center of the cyclase. The criterion for the first sphere is the distance from the ligand 2-azasqualene, which is specified in a published x-ray structure (pdb: 1 ump). These residues were determined automatically using a computer program (http://ligin.weizmann.ac.il/cgi-bin/lpccsu/LpcCsu.cgi; Sobolev V, Sorokine A, Prilusky J, Abola E E, Edelman M. Automated analysis of interatomic contacts in proteins. Bioinformatics 1999; 15(4):327-332.). This program assumes that two molecules are in contact with each other when the distance between their atoms corresponds to the sum of their van der Waals radii±1 Å. The second sphere includes all amino acids which are located within a radius of 5 Å to each residue of the first sphere. Such residues therefore appear to be especially suitable for undertaking directed mutation so as to further modify the enzymatic activity in a targeted fashion.

A "cyclase activity" which has been determined under standard conditions with geranyllinalool of the formula (I), in particular E,E-geranyllinalool, as reference substrate is an enzymatic activity which describes the formation of a cyclic reaction product.

"Standard conditions" are, for example, substrate concentrations of from 10 mM to 0.2 M, in particular 15 to 100 mM, such as, for example, approximately 20 to 25 mM; at pH 4 to 8; and at temperatures of, for example, from 15 to 45 or 20 to 25° C. They can be determined using recombinant cyclase-expressing cells, disrupted cyclase-expressing cells, fractions of these or enriched or purified cyclase enzyme. A reference substrate is, in particular, geranyllinalool, of the formula (I); in particular E,E-geranyllinalool in a concentration of from 15 to 100 mM or approximately 20 to 25 mM, at 20 to 25° C. and pH 6-7, such as, for example, 6.5; as is also described in greater detail in the examples.

Generally also comprised in accordance with the invention are all isomeric forms of the compounds described herein, such as constitutional isomers and in particular stereoisomers and mixtures of these, such as, for example, optical isomers or geometric isomers, such as E- and Z-isomers, and combinations of these. If several centers of asymmetry are present in a molecule, then the invention comprises all combinations of different conformations of these centers of asymmetry, such as, for example, pairs of enantiomers, or any mixtures of stereoisomeric forms.

B. Specific developments of the invention

The present invention relates in particular to the following specific embodiments:

1. A compound of the formula (II)

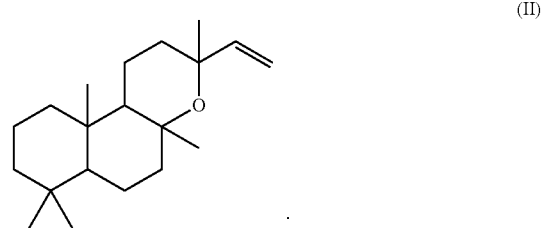 [SMILES: C=CC1(C)CCC2C(C)(CCC3C(C)(C)CCCC32C)O1]

(II)

in stereoisomerically pure form and as a mixture comprising at least one of the possible stereoisomers of this compound.

2. A compound as per embodiment 1 in the form of a mixture which comprises a plurality of stereoisomers of the compound of the formula (II).

3. A compound as per any of the preceding embodiments, which is present in the form of a stereoisomer.

4. A process for the biocatalytic cyclization of a compound of the formula (I)

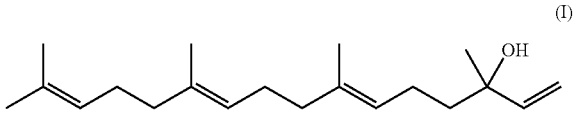 [SMILES: C=CC(C)(O)CC/C=C(\C)CC/C=C(\C)CCC=C(C)C]

(I)

in the presence of a cyclase which has an amino acid sequence as shown in SEQ ID No. 2 or which has at least 80%, 81%, 82%, 83%, 84%, 85%, 86%, 87%, 88%, 89%, 90%, 91%, 92%, 93%, 94%, 95%, 96%, 97%, 98% or 99% sequence identity to SEQ ID No. 2, wherein at least one compound of the formula (I) is bought into contact with the cyclase in a liquid, in particular in a single-phase aqueous or in a two-phase aqueous-organic reaction medium, in particular under conditions which do not adversely affect the desired reaction, and especially under conditions which favour the desired reaction. Suitable reaction conditions (such as, for example, optimal concentration of substrate, enzyme, pH, nature of the buffer which is optionally used, temperature and duration of the reaction, organic solvent) can readily be determined by a person of average skill in the art on the basis of fewer preliminary tests.

5. A process as per embodiment 4, wherein the compound of the formula (I) is employed in the form of a mixture of both enantiomers.

6. A process as per embodiment 5, wherein the mixture is a racemic mixture.

7. A process as per embodiment 5, wherein one of the two enantiomers in the mixture is present in an excess.

8. A process as per any of the embodiments 4 to 7, wherein the compound of the formula (I) is reacted to give the compound of the formula (II).

9. A process as per any of the embodiments 4 to 8, wherein the cyclase is present in crude, purified, dissolved, dispersed or immobilized form, or in the presence of cyclase-displaying cells of a microorganism.

10. A process as per any of the embodiments 4 to 9, wherein the cyclase is present in a form selected from among:
   a) free, optionally purified or partially purified cyclase;
   b) immobilized cyclase;
   c) cyclase, isolated from cells, as per a) or b);
   d) intact, optionally recombinant, cells, optionally quiescent or disrupted cyclase-comprising cells;
   e) cell lysate or cell homogenate of the cells described under d).
11. A process as per any of the embodiments 4 to 10 in the presence of a recombinant microorganism which includes a nucleotide sequence which codes for the cyclase.
12. A process as per embodiment 11, wherein the nucleotide sequence is part of an expression cassette and, therein, is under the control of at least one regulatory sequence.
13. A process as per embodiment 12, wherein the expression cassette is part of an expression vector.
14. A process as per claim 13, wherein the expression vector is selected from among plasmids.
15. A process as per any of the embodiments 4 to 14, wherein the microorganism is selected from among bacteria, fungi and yeasts.
16. A process as per any of the embodiments 4 to 15, wherein the microorganism is selected from among the species *Escherichia coli, Pseudomonas putida, Burkholderia glumae, Corynebacterium glutamicum, Saccharomyces cerevisiae, Pichia pastoris, Streptomyces lividans, Streptomyces coelicolor, Bacillus subtilis* and *Zymomonas mobilis*.
17. A process as per any of the embodiments 4 to 16, wherein the microorganism is *E. coli*.
18. A process as per any of the embodiments 4 to 17, wherein the biocatalytic cyclization takes place in single-phase aqueous systems or in two-phase systems; or in anhydrous systems, such as in ionic fluids or deep eutectic solvents.
19. A process as per any of the embodiments 4 to 18, wherein the biocatalytic cyclization takes place at a temperature in the range of from 20 to 45° C. and/or a pH in the range of from 4 to 8.

C. Further developments of the invention

1. Cyclases Employed in the Process According to the Invention

The present invention is not limited to processes in which the cyclase disclosed herein specifically is employed, but, rather, also extends to processes carried out using functional equivalents of the specifically described cyclase.

Within the scope of the present invention, "functional equivalents" or analogs of the specifically disclosed enzymes and enzyme mutants (derived from SEQ ID No. 2) are polypeptides which differ from them and which also retain the desired cyclase activity.

Thus, for example, "functional equivalents" include enzymes and mutants which, in a used test for "cyclase activity" for the purposes of the invention (i.e. with a reference substrate under standard conditions), display an activity of an enzyme which is by at least 1%, in particular by at least approximately 5 to 10%, such as, for example, by at least 10% or at least 20%, such as, for example, by at least 50% or 75% or 90% higher or lower, comprising a herein specifically defined amino acid sequence derived from SEQ ID No. 2.

The activity data for functional equivalents relate in the present text, unless otherwise specified, to activity determinations carried out by means of a reference substrate, such as under "standard conditions", as defined herein.

The "cyclase activity" for the purposes of the invention can be determined with the aid of a test using the reference substrate, such as, for example, geranyllinalool, under standard conditions as described hereinabove and illustrated in the experimental part.

Functional equivalents are furthermore stable for example between pH 4 to 11 and advantageously have a pH optimum in a range of from pH 5 to 10, such as in particular 6.5 to 9.5 or 7 to 8 or approximately at 7.5, and a temperature optimum in the range of from 15° C. to 80° C. or 20° C. to 70° C., such as, for example, 30 to 60° C. or approximately 35 to 45° C., such as, for example, at 40° C.

"Functional equivalents" in the above sense are also "precursors" of the described polypeptides and "functional derivatives" and "salts" of the polypeptides.

"Functional equivalents" comprise the mutants obtainable by one or more, such as, for example, 1 to 50, 2 to 30, 2 to 15, 4 to 12 or 5 to 10 "mutations", such as amino acid additions, substitutions, deletions and/or inversions, where the abovementioned modifications may occur in any sequence position as long as they lead to a mutant with the property profile in accordance with the invention. Functional equivalence prevails in particular also when the reactivity profiles between mutant and unmodified polypeptide coincide in terms of quality, i.e. when, for example, the identical substrates are reacted at a different rate.

Nonlimiting examples of suitable amino acid substitutions are compiled in the table which follows:

| Original residue | Examples of substitution |
|---|---|
| Ala | Ser |
| Arg | Lys |
| Asn | Gln; His |
| Asp | Glu |
| Cys | Ser |
| Gln | Asn |
| Glu | Asp |
| Gly | Pro |
| His | Asn; Gln |
| Ile | Leu; Val |
| Leu | Ile; Val |
| Lys | Arg; Gln; Glu |
| Met | Leu; Ile |
| Phe | Met; Leu; Tyr |
| Ser | Thr |
| Thr | Ser |
| Trp | Tyr |
| Tyr | Trp; Phe |
| Val | Ile; Leu |

"Precursors" in this context are natural or synthetic precursors of the polypeptides with or without the desired biological activity.

The term "salts" is understood as meaning not only salts of carboxyl groups, but also acid addition salts of amino groups of the cyclase. Salts of carboxyl groups can be generated in a manner known per se and comprise inorganic salts, such as, for example, sodium, calcium, ammonium, iron and zinc salts, and salts with organic bases such as, for example, amines, such as triethanolamine, arginine, lysine, piperidine and the like. Acid addition salts, such as, for example, salts with mineral acids, such as hydrochloric acid or sulfuric acid and salts with organic acids, such as acetic acid and oxalic acid, are likewise subject matter of the invention.

"Functional derivatives" of the cyclase can likewise be generated with the aid of known techniques, either on functional amino acid side groups or at their N- or C-terminal end. Such derivatives comprise for example aliphatic esters of carboxylic acid groups, amides of carboxylic acid groups, obtainable by reaction with ammonia or with a primary or secondary amine; N-acyl derivatives of free amino groups, prepared by reaction with acyl groups; or O-acyl derivatives of free hydroxyl groups, prepared by reaction with acyl groups.

"Functional equivalents" naturally also comprise polypeptides which are available from other organisms, and naturally occurring variants. For example, areas of homologous sequence regions may be established by sequence comparison, and equivalent enzymes can be determined based on the specific information of the invention.

"Functional equivalents" likewise comprise fragments, preferably individual domains or sequence motifs, of the cyclase, which have for example the desired biological function.

"Functional equivalents" are furthermore fusion proteins which have one of the aforementioned polypeptide sequences or functional equivalents thereof and at least one further, functionally different, heterologous sequence in functional N- or C-terminal linkage (i.e. without mutual substantial functional impairment of the fusion protein moieties). Nonlimiting examples of heterologous sequences of this kind are, for example, signal peptides, histidine anchors or enzymes.

If a protein glycosylation is possible, the cyclases comprise "functional equivalents" in deglycosylated or glycosylated form and modified forms which are available by altering the glycosylation pattern.

Cyclase homologs can be generated by mutagenesis, for example by point mutation, extension or truncation of the protein.

Homologs of the proteins according to the invention may be identified by screening combinatorial libraries of mutants, such as, for example, truncated mutants. For example, a variegated library of protein variants can be generated by combinatorial mutagenesis at the nucleic acid level, such as, for example, by enzymatically ligating a mixture of synthetic oligonucleotides. A multiplicity of methods exist which can be used for generating libraries of potential homologs from a degenerate oligonucleotide sequence. The chemical synthesis of a degenerate gene sequence may be carried out in an automatic DNA synthesizer, and the synthetic gene can then be ligated into a suitable expression vector. The use of a degenerate set of genes makes it possible to provide, in a mixture, all sequences which code for the desired set of potential protein sequences. Processes for synthesizing degenerate oligonucleotides are known to the skilled worker (for example Narang, S. A. (1983) Tetrahedron 39:3; Itakura et al. (1984) Annu. Rev. Biochem. 53:323; Itakura et al., (1984) Science 198:1056; Ike et al. (1983) Nucleic Acids Res. 11:477).

A plurality of techniques for screening gene products of combinatorial libraries which have been generated by point mutations or truncation and for screening cDNA libraries for gene products with a selected property are known in the art. These techniques may be adapted to the rapid screening of the gene libraries which have been generated by combinatorial mutagenesis of homologs according to the invention. The most frequently used techniques for screening large gene libraries, as the basis for high-throughput analysis, comprise cloning the gene library into replicatable expression vectors, transforming the suitable cells with the resulting vector library and expressing the combinatorial genes under conditions under which the detection of the desired activity facilitates the isolation of the vector which codes for the gene whose product has been detected. Recursive ensemble mutagenesis (REM), a technique which increases the frequency of functional mutants in the libraries, may be used in combination with the screening tests for identifying homologs (Arkin and Yourvan (1992) PNAS 89:7811-7815; Delgrave et al. (1993) Protein Engineering 6(3):327-331).

"Functional equivalents" which are also comprised in accordance with the invention are homologs to the specifically disclosed proteins. These have at least 60%, preferably at least 75%, in particular at least 85%, such as, for example, 90, 91, 92, 93, 94, 95, 96, 97, 98 or 99%, homology (or identity) to one of the specifically disclosed amino acid sequences, calculated by the algorithm of Pearson and Lipman, Proc. Natl. Acad, Sci. (USA) 85(8), 1988, 2444-2448. A homology or identity, expressed as a percentage, of a homologous polypeptide according to the invention means in particular an identity, expressed as a percentage, of the amino acid residues based on the total length of one of the amino acid sequences described specifically herein.

The identity data, expressed as a percentage, may also be determined with the aid of BLAST alignments, algorithm blastp (protein-protein BLAST), or by applying the Clustal settings specified hereinbelow.

2. Nucleic acids and constructs 2.1 Nucleic acids

The process according to the invention can be carried out in the presence of a microorganism which includes a nucleotide sequence, that is to say a nucleic acid molecule, which codes for the cyclase.

All the nucleic acid molecules mentioned herein (single- and double-stranded DNA and RNA sequences such as, for example, cDNA and mRNA) can be prepared in a manner known per se by chemical synthesis from the nucleotide building blocks, such as, for example, by fragment condensation of individual overlapping, complementary nucleic acid building blocks of the double helix. The chemical synthesis of oligonucleotides can be effected for example in a known manner by the phosphoamidite method (Voet, Voet, $2^{nd}$ Edition, Wiley Press New York, pages 896-897). The adding-on of synthetic oligonucleotides and filling-in of gaps with the aid of the Klenow fragment of the DNA polymerase and ligation reactions as well as general cloning methods are described in Sambrook et al. (1989), Molecular Cloning: A laboratory manual, Cold Spring Harbor Laboratory Press.

One differentiates between isolated nucleic acid molecules which code for the cyclase or biologically active segments thereof and nucleotide fragments, which may be used for example for use as hybridization probes or primers for identifying or amplifying cyclase-encoding nucleic acids.

The nucleic acid molecules may additionally comprise untranslated sequences of the 3'- and/or 5'-terminus of the coding gene region.

Nucleic acid molecules or segments thereof which are complementary to the specifically described nucleotide sequences exist.

The nucleotide sequences make it possible to generate probes and primers which may be used for identifying and/or cloning homologous sequences in other types of cells and organisms. Such probes or primers usually comprise a nucleotide sequence region which, under "stringent" conditions (see hereinbelow), hybridizes to at least approximately 12, preferably at least approximately 25, such as, for example, approximately 40, 50 or 75, contiguous nucleotides of a sense strand of the nucleic acid sequence or of a corresponding antisense strand.

An "isolated" nucleic acid molecule is separated from other nucleic acid molecules which are present in the natural source of the nucleic acid and may in addition be essentially free from other cellular material or culture medium, if prepared by recombinant techniques, or free from chemical precursors or other chemicals if chemically synthesized.

The nucleic acid molecule can be isolated by means of standard techniques of molecular biology and the sequence information provided. For example, cDNA can be isolated from a suitable cDNA library by using one of the specifically disclosed complete sequences or a segment thereof as hybridization probe and standard hybridization techniques (as described for example in Sambrook, J., Fritsch, E. F. and Maniatis, T. Molecular Cloning: A Laboratory Manual. $2^{nd}$ Ed., Cold Spring Harbor Laboratory, Cold Spring Harbor Laboratory Press, Cold Spring Harbor, N.Y., 1989). Moreover, a nucleic acid molecule comprising one of the disclosed sequences or a segment thereof can be isolated by polymerase chain reaction, with the oligonucleotide primers which have been generated on the basis of this sequence being used. The nucleic acid amplified thus can be cloned into a suitable vector and characterized by DNA sequence analysis. The oligonucleotides can furthermore be prepared by standard synthetic methods, for example using an automatic DNA synthesizer.

Nucleic acid sequences or derivatives thereof, homologs or parts of these sequences can be isolated from other bacteria for example using customary hybridization methods or the PCR technology, for example via genomic libraries or cDNA libraries. These DNA sequences hybridize under standard conditions to the sequences according to the invention.

"To hybridize" is understood as meaning the ability of a poly- or oligonucleotide to bind to an almost complementary sequence under standard conditions, while nonspecific binding between noncomplementary partners does not occur under these conditions. To this end, the sequences may be 90-100% complementary. The property of complementary sequences of being able to specifically bind to one another is exploited for example in the Northern or Southern Blot technique or in primer binding in PCR or RT-PCR.

For the hybridization, it is advantageous to use short oligonucleotides of the conserved regions. However, longer fragments of the nucleic acids according to the invention or the complete sequences may also be used for the hybridization. Depending on the nucleic acid used (oligonucleotide, longer fragment or complete sequence), or depending on which type of nucleic acid, DNA or RNA, is used for the hybridization, these standard conditions vary. Thus, for example, the melting temperatures for DNA:DNA hybrids are by approximately 10° C. lower than those of DNA:RNA hybrids of the same length.

Depending on the nucleic acid, standard conditions are understood as meaning, for example, temperatures of between 42 and 58° C. in an aqueous buffer solution with a concentration of between 0.1 to 5×SSC (1×SSC=0.15 M NaCl, 15 mM sodium citrate, pH 7.2) or additionally in the presence of 50% formamide such as, for example, 42° C. in 5×SSC, 50% formamide. Advantageously, the hybridization conditions for DNA:DNA hybrids are 0.1×SSC and temperatures of between approximately 20° C. to 45° C., preferably between approximately 30° C. to 45° C. For DNA:RNA hybrids, the hybridization conditions are advantageously 0.1×SSC and temperatures of between approximately 30° C. to 55° C., preferably between approximately 45° C. to 55° C. These stated temperatures for the hybridization are examples of calculated melting temperature values for a nucleic acid with a length of approximately 100 nucleotides and a G+C content of 50% in the absence of formamide. The experimental conditions for the DNA hybridization are described in relevant textbooks on genetics, such as, for example, Sambrook et al., "Molecular Cloning", Cold Spring Harbor Laboratory, 1989, and can be calculated using formulas known by a person skilled in the art, for example as a function of the length of the nucleic acids, the type of the hybrids or the G+C content. Further information on hybridization can be obtained by a person skilled in the art from the following textbooks: Ausubel et al. (eds), 1985, Current Protocols in Molecular Biology, John Wiley & Sons, New York; Hames and Higgins (eds), 1985, Nucleic Acids Hybridization: A Practical Approach, IRL Press at Oxford University Press, Oxford; Brown (ed), 1991, Essential Molecular Biology: A Practical Approach, IRL Press at Oxford University Press, Oxford.

The "hybridization" may take place in particular under stringent conditions. Such hybridization conditions are described, for example, by Sambrook, J., Fritsch, E. F., Maniatis, T., in: Molecular Cloning (A Laboratory Manual), $2^{nd}$ Edition, Cold Spring Harbor Laboratory Press, 1989, pages 9.31-9.57 or in Current Protocols in Molecular Biology, John Wiley & Sons, N.Y. (1989), 6.3.1-6.3.6.

"Stringent" hybridization conditions are taken to mean in particular: incubation at 42° C. over night in a solution consisting of 50% formamide, 5×SSC (750 mM NaCl, 75 mM trisodium citrate), 50 mM sodium phosphate (pH 7.6), 5×Denhardt's solution, 10% dextran sulfate and 20 g/ml denatured, sheared salmon sperm DNA, followed by a step of washing the filters with 0.1×SSC at 65° C.

The nucleotide sequences may be fused to promoters. The promoters, which are arranged upstream of the specified nucleotide sequences, may have been changed by at least one nucleotide substitution, at least one insertion, inversion and/or deletion, without, however, adversely affecting the functionality/activity of the promoters. Moreover, the efficacy of the promoters may be enhanced by modifying their sequence, or the promoters may be exchanged completely for more effective promoters, also from foreign organisms.

"Identity" between two nucleic acids is understood as meaning the identity of the nucleotides over the in each case entire length of the nucleic acid, in particular the identity which is calculated by comparison with the aid of the Vector NTI Suite 7.1 software from Informax (USA) using the Clustal method (Higgins D C, Sharp P M. Fast and sensitive multiple sequence alignments on a microcomputer. Comput Appl. Biosci. 1989 April; 5(2):151-1), setting the following parameters:

Multiple alignment parameters:

| | |
|---|---|
| Gap opening penalty | 10 |
| Gap extension penalty | 10 |
| Gap separation penalty range | 8 |
| Gap separation penalty | off |
| % identity for alignment delay | 40 |
| Residue specific gaps | off |
| Hydrophilic residue gap | off |
| Transition weighting | 0 |

Pairwise alignment parameter:

| | |
|---|---|
| FAST algorithm | on |
| K-tuplesize | 1 |
| Gap penalty | 3 |
| Window size | 5 |
| Number of best diagonals | 5 |

As an alternative, the identity may also be determined according to Chenna, Ramu, Sugawara, Hideaki, Koike, Tadashi, Lopez, Rodrigo, Gibson, Toby J, Higgins, Desmond G, Thompson, Julie D. Multiple sequence alignment with the Clustal series of programs. (2003) Nucleic Acids Res 31 (13):3497-500, according to the website http://www.ebi.ac.uk/Tools/clustalw/index.html# and using the following parameters:

| | |
|---|---|
| DNA Gap Open Penalty | 15.0 |
| DNA Gap Extension Penalty | 6.66 |
| DNA Matrix | Identity |
| Protein Gap Open Penalty | 10.0 |
| Protein Gap Extension Penalty | 0.2 |
| Protein matrix | Gonnet |
| Protein/DNA ENDGAP | −1 |
| Protein/DNA GAPDIST | 4 |

2.2 Generation of functional mutants

Moreover, a person skilled in the art is familiar with methods for generating functional mutants, that is to say nucleotide sequences which code for a cyclase with at least 80%, 81%, 82%, 83%, 84%, 85%, 86%, 87%, 88%, 89%, 90%, 91%, 92%, 93%, 94%, 95%, 96%, 97%, 98% or 99% sequence identity to SEQ ID No. 2.

Depending on the technique used, a person skilled in the art can introduce entirely random or else more directed mutations into genes or else noncoding nucleic acid regions (which are for example important for regulating expression) and subsequently generate genetic libraries. The methods of molecular biology required for this purpose are known to the skilled worker and for example described in Sambrook and Russell, Molecular Cloning. 3rd Edition, Cold Spring Harbor Laboratory Press 2001.

Methods for modifying genes and thus for modifying the protein encoded by them have been known to the skilled worker for a long time, such as, for example
- site-specific mutagenesis, where individual or several nucleotides of a gene are replaced in a directed fashion (Trower M K (Ed.) 1996; In vitro mutagenesis protocols. Humana Press, New Jersey),
- saturation mutagenesis, in which a codon for any amino acid can be exchanged or added at any point of a gene (Kegler-Ebo D M, Docktor C M, DiMaio D (1994) Nucleic Acids Res 22:1593; Barettino D, Feigenbutz M, Valcárel R, Stunnenberg H G (1994) Nucleic Acids Res 22:541; Bark S (1995) Mol Biotechnol 3:1),
- error-prone polymerase chain reaction, where nucleotide sequences are mutated by error-prone DNA polymerases (Eckert K A, Kunkel T A (1990) Nucleic Acids Res 18:3739);
- the SeSaM method (sequence saturation method), in which preferred exchanges are prevented by the polymerase. Schenk et al., Biospektrum, Vol. 3, 2006, 277-279
- the passaging of genes in mutator strains, in which, for example owing to defective DNA repair mechanisms, there is an increased mutation rate of nucleotide sequences (Greener A, Callahan M, Jerpseth B (1996) An efficient random mutagenesis technique using an E. coli mutator strain. In: Trower M K (Ed.) In vitro mutagenesis protocols. Humana Press, New Jersey), or
- DNA shuffling, in which a pool of closely related genes is formed and digested and the fragments are used as templates for a polymerase chain reaction in which, by repeated strand separation and reassociation, full-length mosaic genes are ultimately generated (Stemmer W P C (1994) Nature 370:389; Stemmer W P C (1994) Proc Natl Acad Sci USA 91:10747).

Using so-called directed evolution (described, inter alia, in Reetz M T and Jaeger K-E (1999), Topics Curr Chem 200:31; Zhao H, Moore J C, Volkov A A, Arnold F H (1999), Methods for optimizing industrial enzymes by directed evolution, In: Demain A L, Davies J E (Ed.) Manual of industrial microbiology and biotechnology. American Society for Microbiology), a skilled worker can produce functional mutants in a directed manner and on a large scale. To this end, in a first step, gene libraries of the respective proteins are first produced, for example using the methods given above. The gene libraries are expressed in a suitable way, for example by bacteria or by phage display systems.

The relevant genes of host organisms which express functional mutants with properties that largely correspond to the desired properties can be submitted to another mutation cycle. The steps of the mutation and selection or screening can be repeated iteratively until the present functional mutants have the desired properties to a sufficient extent. Using this iterative procedure, a limited number of mutations, for example 1, 2, 3, 4 or 5 mutations, can be performed in stages and assessed and selected for their influence on the enzyme property in question. The selected mutant can then be submitted to a further mutation step in the same way. In this way, the number of individual mutants to be investigated can be reduced significantly.

The results according to the invention also provide important information relating to structure and sequence of the relevant enzymes, which is required for generating, in a targeted fashion, further enzymes with desired modified properties. In particular, it is possible to define so-called "hot spots", i.e. sequence segments that are potentially suitable for modifying an enzyme property by introducing targeted mutations.

Information can also be deduced regarding amino acid sequence positions, in the region of which mutations can be effected that should probably have little effect on the enzyme activity, and can be designated as potential "silent mutations".

2.3 Constructs

In the process according to the invention, the nucleotide sequence may be part of an expression cassette. The terms expression cassette and expression construct are used synonymously. The preferably recombinant expression construct contains a nucleic acid sequence which encodes a polypeptide according to the invention and which is under genetic control of regulatory nucleic acid sequences.

In the process according to the invention, the expression cassette may be part of an expression vector, in particular of a recombinant expression vector.

An "expression unit" is understood as meaning, in accordance with the invention, a nucleic acid with expression activity which comprises a promoter as defined herein and, after functional linkage with a nucleic acid to be expressed or a gene, regulates the expression, i.e. the transcription and the translation of said nucleic acid or said gene. It is therefore in this connection also referred to as a "regulatory nucleic acid sequence". In addition to the promoter, other regulatory elements, for example enhancers, can also be present.

An "expression cassette" or "expression construct" is understood as meaning, in accordance with the invention, an expression unit which is functionally linked to the nucleic acid to be expressed or the gene to be expressed. In contrast to an expression unit, an expression cassette therefore comprises not only nucleic acid sequences which regulate transcription and translation, but also the nucleic acid sequences that are to be expressed as protein as a result of transcription and translation.

The terms "expression" or "overexpression" describe, in the context of the invention, the production or increase in intracellular activity of one or more enzymes in a microorganism, which are encoded by the corresponding DNA. To this end, it is possible for example to introduce a gene into an organism, replace an existing gene with another gene, increase the copy number of the gene(s), use a strong promoter or use a gene which encodes for a corresponding enzyme with a high activity; optionally, these measures can be combined.

Preferably such constructs according to the invention comprise a promoter 5'-upstream of the respective coding sequence and a terminator sequence 3'-downstream and optionally other usual regulatory elements, in each case in operative linkage with the coding sequence.

A "promoter", a "nucleic acid with promoter activity" or a "promoter sequence" is understood as meaning, in accordance with the invention, a nucleic acid which, when functionally linked to a nucleic acid to be transcribed, regulates the transcription of said nucleic acid.

In this context, a "functional" or "operative" linkage is understood as meaning for example the sequential arrangement of one of the nucleic acids with promoter activity and of a nucleic acid sequence to be transcribed and optionally further regulatory elements, for example nucleic acid sequences which ensure the transcription of nucleic acids, and for example a terminator, in such a way that each of the regulatory elements can perform its function upon transcription of the nucleic acid sequence. This does not necessarily require a direct linkage in the chemical sense. Genetic control sequences, for example enhancer sequences, can even exert their function on the target sequence from more remote positions or even from other DNA molecules. Preferred arrangements are those in which the nucleic acid sequence to be transcribed is positioned behind (i.e. at the 3'-end of) the promoter sequence so that the two sequences are joined together covalently. The distance between the promoter sequence and the nucleic acid sequence to be expressed recombinantly can be smaller than 200 base pairs, or smaller than 100 base pairs or smaller than 50 base pairs.

In addition to promoters and terminator, the following may be mentioned as examples of other regulatory elements: targeting sequences, enhancers, polyadenylation signals, selectable markers, amplification signals, replication origins and the like. Suitable regulatory sequences are described, for example, in Goeddel, Gene Expression Technology: Methods in Enzymology 185, Academic Press, San Diego, Calif. (1990).

Nucleic acid constructs according to the invention comprise in particular a sequence coding for a cyclase, for example derived from SEQ ID No. 1, or coding for a cyclase as per SEQ ID No. 2 or derivatives and homologs thereof, and the nucleic acid sequences which can be derived therefrom and which have been linked operatively or functionally with one or more regulatory signals, advantageously for controlling, for example increasing, gene expression.

In addition to these regulatory sequences, the natural regulation of these sequences may still be present before the actual structural genes and optionally may have been genetically modified so that the natural regulation has been switched off and expression of the genes has been enhanced. The nucleic acid construct may, however, also be of simpler construction, i.e. no additional regulatory signals have been inserted before the coding sequence and the natural promoter, with its regulation, has not been removed. Instead, the natural regulatory sequence is mutated such that regulation no longer takes place and the gene expression is increased.

A preferred nucleic acid construct advantageously also comprises one or more of the already mentioned "enhancer" sequences in functional linkage with the promoter, which sequences make possible an enhanced expression of the nucleic acid sequence. Additional advantageous sequences may also be inserted at the 3'-end of the DNA sequences, such as further regulatory elements or terminators. One or more copies of the nucleic acids according to the invention may be present in a construct. In the construct, other markers, such as genes which complement auxotrophisms or antibiotic resistances, may also optionally be present so as to select for the construct.

Examples of suitable regulatory sequences are present in promoters such as cos, tac, trp, tet, trp-tet, lpp, lac, lpp-lac, lacIq, T7, T5, T3, gal, trc, ara, rhaP (rhaP$_{BAD}$)SP6, lambda-P$_R$ or in the lambda-P$_L$ promoter, and these are advantageously employed in Gram-negative bacteria. Further advantageous regulatory sequences are present for example in the Gram-positive promoters amy and SPO2, in the yeast or fungal promoters ADC1, MFalpha, AC, P-60, CYC1, GAPDH, TEF, rp28, ADH. Artificial promoters may also be used for regulation.

For expression in a host organism, the nucleic acid construct is inserted advantageously into a vector such as, for example, a plasmid or a phage, which makes possible optimal expression of the genes in the host. Vectors are also understood as meaning, in addition to plasmids and phages, all the other vectors which are known to the skilled worker, that is to say for example viruses such as SV40, CMV, baculovirus and adenovirus, transposons, IS elements, phasmids, cosmids and linear or circular DNA. These vectors are capable of replicating autonomously in the host organism or else chromosomally. These vectors are a further development of the invention.

Suitable plasmids are, for example, in E. coli pLG338, pACYC184, pBR322, pUC18, pUC19, pKC30, pRep4, pHS1, pKK223-3, pDHE19.2, pHS2, pPLc236, pMBL24, pLG200, pUR290, pIN-III$^{113}$-B1, λgt11 or pBdCI, in Streptomyces pIJ101, pIJ364, pIJ702 or pIJ361, in Bacillus pUB110, pC194 or pBD214, in Corynebacterium pSA77 or pAJ667, in fungi pALS1, pIL2 or pBB116, in yeasts 2alphaM, pAG-1, YEp6, YEp13 or pEMBLYe23 or in plants pLGV23, pGHlac⁺, pBIN19, pAK2004 or pDH51. The abovementioned plasmids are a small selection of the plasmids which are possible. Further plasmids are well known to the skilled worker and can be found for example in the book Cloning Vectors (Eds. Pouwels P. H. et al. Elsevier, Amsterdam-New York-Oxford, 1985, ISBN 0 444 904018).

In a further development of the vector, the vector which comprises the nucleic acid construct according to the invention or the nucleic acid according to the invention can advantageously also be introduced into the microorganisms in the form of a linear DNA and integrated into the host organisms's genome via heterologous or homologous recombination. This linear DNA can consist of a linearized vector such as a plasmid or only of the nucleic acid construct or the nucleic acid according to the invention.

For optimal expression of heterologous genes in organisms, it is advantageous to modify the nucleic acid sequences to match the specific "codon usage" used in the organism. The "codon usage" can be determined readily by computer evaluations of other, known genes of the organism in question.

An expression cassette according to the invention is generated by fusing a suitable promoter to a suitable coding nucleotide sequence and a terminator or polyadenylation signal. Customary recombination and cloning techniques are used for this purpose, as are described, for example, in T. Maniatis, E. F. Fritsch and J. Sambrook, Molecular Cloning: A Laboratory Manual, Cold Spring Harbor Laboratory, Cold Spring Harbor, N.Y. (1989) and in T. J. Silhavy, M. L. Berman and L. W. Enquist, Experiments with Gene Fusions, Cold Spring Harbor Laboratory, Cold Spring Harbor, N.Y. (1984) and in Ausubel, F. M. et al., Current Protocols in Molecular Biology, Greene Publishing Assoc. and Wiley Interscience (1987).

For expression in a suitable host organism, the recombinant nucleic acid construct or gene construct is advantageously inserted into a host-specific vector which makes possible optimal expression of the genes in the host. Vectors are well known to the skilled worker and can be found for example in "cloning vectors" (Pouwels P. H. et al., Ed., Elsevier, Amsterdam-New York-Oxford, 1985).

3. Microorganisms

Depending on the context, the term "microorganism" may refer to the wild-type microorganism or to a genetically modified, recombinant microorganism, or to both.

With the aid of the vectors according to the invention it is possible to generate recombinant microorganisms which are transformed for example with at least one vector according to the invention and which can be employed for the production of the polypeptides according to the invention. Advantageously, the above-described recombinant constructs according to the invention are introduced into a suitable host system and expressed therein. In this context, customary cloning and transfection methods which are known to the skilled worker, such as, for example, coprecipitation, protoplast fusion, electroporation, retroviral transfection and the like, are preferably used so as to allow expression of the abovementioned nucleic acids in the expression system in question. Suitable systems are described for example in Current Protocols in Molecular Biology, F. Ausubel et al., Ed., Wiley Interscience, New York 1997, or Sambrook et al. Molecular Cloning: A Laboratory Manual. $2^{nd}$ Ed., Cold Spring Harbor Laboratory, Cold Spring Harbor Laboratory Press, Cold Spring Harbor, N.Y., 1989.

Suitable recombinant host organisms for the nucleic acid according to the invention or the nucleic acid construct are, in principle, all prokaryotic or eukaryotic organisms. Microorganisms such as bacteria, fungi or yeasts are advantageously used as host organisms. Gram-positive or Gram-negative bacteria, preferably bacteria from the families Enterobacteriaceae, Pseudomonadaceae, Rhizobiaceae, Streptomycetaceae or Nocardiaceae, especially preferably bacteria from the genera *Escherichia, Pseudomonas, Streptomyces, Nocardia, Burkholderia, Salmonella, Agrobacterium, Clostridium* or *Rhodococcus*, are advantageously used. Very especially preferred is the genus and species *Escherichia coli*. Further advantageous bacteria can additionally be found in the group of the alpha-proteobacteria, beta-proteobacteria or gamma-proteobacteria.

In this context, the host organism(s) according to the invention contain(s) preferably at least one of the nucleic acid sequences, nucleic acid constructs or vectors which are described in the present invention and which code for an enzyme with phenylethanol dehydrogenase activity as defined hereinabove.

Depending on the host organism, the organisms used in the process according to the invention are grown or cultured in a manner with which the skilled worker is familiar. As a rule, microorganisms are grown in a liquid medium which comprises a carbon source, usually in the form of sugars, a nitrogen source, usually in the form of organic nitrogen sources such as yeast extract or salts such as ammonium sulfate, trace elements such as iron salts, manganese salts, magnesium salts and optionally vitamins, at temperatures of between 0° C. and 100° C., preferably between 10° C. to 60° C., while passing in oxygen gas. The pH of the liquid medium may be maintained at a fixed value, that is to say may be regulated during culturing, or not. Culturing may take place batchwise, semibatchwise or continuously. Nutrients may be provided at the beginning of the fermentation or fed in semicontinuously or continuously.

4. Recombinant Production of Enzymes According to the Invention

The invention furthermore relates to processes for the recombinant production of enzymes according to the invention or functional biologically active fragments thereof, wherein an enzyme-producing microorganism is cultured, the expression of the polypeptides is optionally induced, and the polypeptides are isolated from the culture. If desired, the polypeptides can also be produced on an industrial scale in this manner.

The microorganisms produced thus may be cultured continuously or discontinuously by the batch method or the fed-batch method or the repeated fed-batch method. An overview of known cultivation methods can be found in the textbook by Chmiel (Bioprozeβtechnik 1. Einführung in die Bioverfahrenstechnik [Bioprocess technology 1. Introduction to bioprocess technology] (Gustav Fischer Verlag, Stuttgart, 1991)) or in the textbook by Storhas (Bioreaktoren and periphere Einrichtungen [Bioreactors and peripheral equipment] (Vieweg Verlag, Braunschweig/Wiesbaden, 1994)).

The culture medium to be used must suitably meet the requirements of the respective strains. Descriptions of culture media for various microorganisms are given in the manual "Manual of Methods for General Bacteriology" of the American Society for Bacteriology (Washington D. C., USA, 1981).

These media which can be used in accordance with the invention usually comprise one or more carbon sources, nitrogen sources, inorganic salts, vitamins and/or trace elements.

Preferred carbon sources are sugars, such as mono-, di- or polysaccharides. Very good carbon sources are, for example, glucose, fructose, mannose, galactose, ribose, sorbose, ribulose, lactose, maltose, sucrose, raffinose, starch or cellulose. Sugars can also be added to the media via complex compounds, such as molasses, or other by-products of sugar refining. It can also be advantageous to add mixtures of different carbon sources. Other possible carbon sources are oils and fats, for example soya oil, sunflower oil, peanut oil, and coconut fat, fatty acids such as, for example, palmitic acid, stearic acid or linoleic acid, alcohols, for example glycerol, methanol or ethanol, and organic acids, for example acetic acid or lactic acid.

Nitrogen sources are usually organic or inorganic nitrogen compounds or materials that comprise these compounds. Examples of nitrogen sources comprise ammonia gas or ammonium salts, such as ammonium sulfate, ammonium chloride, ammonium phosphate, ammonium carbonate or ammonium nitrate, nitrates, urea, amino acids or complex nitrogen sources, such as cornsteep liquor, soya meal, soya protein, yeast extract, meat extract and others. The nitrogen sources may be used individually or as a mixture.

Inorganic salt compounds that can be present in the media comprise the chloride, phosphorus or sulfate salts of calcium, magnesium, sodium, cobalt, molybdenum, potassium, manganese, zinc, copper and iron.

Inorganic sulfur-comprising compounds, for example sulfates, sulfites, dithionites, tetrathionates, thiosulfates, sulfides as well as organic sulfur compounds, such as mercaptans and thiols, may be used as the sulfur source.

Phosphoric acid, potassium dihydrogen phosphate or dipotassium hydrogen phosphate or the corresponding sodium-comprising salts may be used as the phosphorus source.

Chelating agents may be added to the medium in order to keep the metal ions in solution. Especially suitable chelating agents comprise dihydroxyphenols, such as catechol or protocatechuate, or organic acids, such as citric acid.

The fermentation media used in accordance with the invention usually also comprise other growth factors such as vitamins or growth promoters, which include for example biotin, riboflavin, thiamine, folic acid, nicotinic acid, panthothenate and pyridoxine. Growth factors and salts often originate from the components of complex media, such as yeast extract, molasses, corn steep liquor and the like. Moreover, suitable precursors can be added to the culture medium. The exact composition of the compounds in the medium depends greatly on the respective experiment and is decided for each specific case individually. Information on media optimization can be found in the textbook "Applied Microbiol. Physiology, A Practical Approach" (Ed. P. M. Rhodes, P. F. Stanbury, IRL Press (1997), p. 53-73, ISBN 0 19 963577 3). Growth media can also be obtained from commercial suppliers, such as Standard 1 (Merck) or BHI (brain heart infusion, DIFCO) and the like.

All media components are sterilized, either by heat (20 min at 1.5 bar and 121° C.) or by filter sterilization. The components may be sterilized either together or separately if necessary. All media components may be present at the beginning of a culture or can be added either continuously or batchwise.

The culture temperature is normally between 15° C. and 45° C., preferably 25° C. to 40° C. and can be varied or kept constant during the experiment. The pH of the medium should be in the range of from 5 to 8.5, preferably around 7.0. The pH for growing can be controlled during growing by adding basic compounds such as sodium hydroxide, potassium hydroxide, ammonia or ammonia water, or acidic compounds such as phosphoric acid or sulfuric acid. Antifoams, for example fatty acid polyglycol esters, may be used for controlling foaming. To maintain the stability of plasmids, suitable selectively acting substances, such as, for example, antibiotics, may be added to the medium. To maintain aerobic conditions, oxygen or oxygen-comprising gas mixtures, such as, for example, ambient air, are passed into the culture. The temperature of the culture is normally in the range of from 20° C. to 45° C. The culture is continued until a maximum of the desired product has formed. This target is normally reached within 10 hours to 160 hours.

The fermentation liquor is subsequently processed further. Depending on the requirements, the biomass may be removed from the fermentation liquor completely or partially by separation techniques, for example centrifugation, filtration, decanting or a combination of these methods, or may be left in it completely.

If the polypeptides are not secreted into the culture medium, the cells can also be lysed and the product can be obtained from the lysate by known protein isolation methods. The cells can optionally be disrupted with high-frequency ultrasound, high pressure, for example in a French press, by osmolysis, by the action of detergents, lytic enzymes or organic solvents, by means of homogenizers, or by a combination of several of the aforementioned methods.

The polypeptides may be purified by known chromatographic techniques, such as molecular sieve chromatography (gel filtration), such as Q-Sepharose chromatography, ion-exchange chromatography and hydrophobic chromatography, and with other usual techniques such as ultrafiltration, crystallization, salting out, dialysis and native gel electrophoresis. Suitable methods are described, for example, in Cooper, T. G., Biochemische Arbeitsmethoden [Biochemical processes], Verlag Walter de Gruyter, Berlin, New York, or in Scopes, R., Protein Purification, Springer Verlag, New York, Heidelberg, Berlin.

For isolating the recombinant protein, it may be advantageous to use vector systems or oligonucleotides which extend the cDNA by defined nucleotide sequences and therefore code for modified polypeptides or fusion proteins, which for example serve for easier purification. Suitable modifications of this type are, for example, so-called "tags", which function as anchors, for example the modification known as hexa-histidine anchor, or epitopes that can be recognized as antigens of antibodies (described, for example, in Harlow, E. and Lane, D., 1988, Antibodies: A Laboratory Manual. Cold Spring Harbor (N.Y.) Press). These anchors can serve for attaching the proteins to a solid carrier, for example a polymer matrix, which may, for example, be used as packing in a chromatography column, or may be used on a microtiter plate or on some other carrier.

At the same time, these anchors may also be used for recognition of the proteins. For recognition of the proteins, it is furthermore also possible to use usual markers, such as fluorescent dyes, enzyme markers, which form a detectable reaction product after reaction with a substrate, or radioactive markers, alone or in combination with the anchors for derivatization of the proteins.

Analogously, such cyclase-expressing microorganisms may also be employed for the fermentative production of the compounds of the formula II, where compounds of the formula I are additionally added to the medium to act as substrate, and the microorganisms are cultured, and the product of value is optionally isolated from the fermentation liquor. In addition, the compound of the formula (I) may also be produced autonomously by a microorganism, since this microorganism has the corresponding biochemical equipment for the synthesis of (I) from simple precursors.

6. Enzyme immobilization

The enzymes used according to the invention can be used in free or immobilized form in the processes described herein. An immobilized enzyme is an enzyme that is fixed to an inert carrier. Suitable carrier materials and the enzymes immobilized thereon are known from EP-A-1149849, EP-A-1069183 and DE-OS 100193773 and from the references cited therein. In this respect, the disclosure of these documents is incorporated herein in its entirety by reference. The suitable carrier materials include, for example, clays, clay minerals such as kaolinite, diatomaceous earth, perlite, silica, aluminum oxide, sodium carbonate, calcium carbonate, cellulose powder, anion exchanger materials, synthetic polymers, such as polystyrene, acrylic resins, phenol/formaldehyde resins, polyurethanes and polyolefins, such as polyethylene and polypropylene. For making the supported enzymes, the carrier materials are usually employed in finely-divided, particulate form, with porous forms being preferred. The particle size of the carrier material is usually no more than 5 mm, in particular no more than 2 mm (particle-size distribution curve). Similarly, when using the dehydrogenase as a whole-cell catalyst, a free or immobilized form can be selected. Carrier materials are, for example, Ca alginate and carrageenan. Enzymes as well as cells may also be crosslinked directly with glutaraldehyde (cross-linking to CLEAs). Corresponding and other immobilization techniques are described, for example, in J. Lalonde and A. Margolin "Immobilization of Enzymes" in K. Drauz and H. Waldmann, Enzyme Catalysis in Organic Synthesis 2002, Vol. III, 991-1032, Wiley-VCH, Weinheim. Further information on biotransformations and bioreactors for carrying out processes according to the invention are also given, for example, in Rehm et al (Ed.) Biotechology, 2nd Edn., Vol. 3, Chapter 17, VCH, Weinheim.

6. Enzymatic cyclization of geranyllinalool

The cyclization process according to the invention is carried out in particular in the presence of an enzyme, where the enzyme is encoded by a nucleic acid sequence according to SEQ ID No. 1 or a functional equivalent thereof, wherein the nucleic acid sequence is a constituent of a gene construct or vector. Such gene constructs or vectors are described in detail in International application PCT/EP2010/057696 on pages 16 to 20, which is expressly referred to here.

The host cell, which contains a gene construct or a vector, in which the nucleic acid sequence that codes for the enzyme with the desired activity is present is also called a transgenic organism. The generation of such transgenic organisms is known in principle and is discussed for example in International application PCT/EP2010/057696 on page 20, to which reference is expressly made here.

Cells from the group comprising bacteria, cyanobacteria, fungi and yeasts are preferably selected as transgenic organisms. The cell is preferably selected from fungi of the genus *Pichia* or bacteria of the genera *Escherichia, Corynebacterium, Ralstonia, Clostridium, Pseudomonas, Bacillus, Zymomonas, Rhodobacter, Streptomyces, Burkholderia, Lactobacillus* or *Lactococcus*. The cell is especially preferably selected from bacteria of the species *Escherichia coli, Pseudomonas putida, Burkholderia glumae, Streptomyces lividans, Streptomyces coelicolor* or *Zymomonas mobilis*.

Preference is given to a process according to the invention which is characterized in that the enzyme with the activity of a cyclase is encoded by a gene which has been isolated from a microorganism, selected from among *Zymomonas mobilis*.

Preference is furthermore given to a process according to the invention which is characterized in that the enzyme with the cyclase activity has been generated by a microorganism which overproduces the enzyme and which has been selected from the group of the microorganisms consisting of the genera *Escherichia, Corynebacterium, Ralstonia, Clostridium, Pseudomonas, Bacillus, Zymomonas, Rhodobacter, Streptomyces, Burkholderia, Lactobacillus* and *Lactococcus*.

Specific mention is made of a process according to the invention which is characterized in that the enzyme with the cyclase activity has been produced by transgenic microorganisms of the species *Escherichia coli, Pseudomonas putida, Burkholderia glumae, Corynebacterium glutamicum, Saccharomyces cerevisiae, Pichia pastoris, Streptomyces lividans, Streptomyces coelicolor, Bacillus subtilis* or *Zymomonas mobilis*, which overproduce the enzyme with the cyclase activity.

The process according to the invention is characterized in that the enzyme is present in at least one of the following forms:
a) free, optionally purified or partially purified polypeptide;
b) immobilized polypeptide;
c) polypeptide, isolated from cells, as per a) or b);
d) intact cell, optionally quiescent or growing cells comprising at least one such polypeptide;
e) lysate or homogenate of the cells described under d).

A further embodiment of the process according to the invention is characterized in that the cells are microorganisms, preferably transgenic microorganisms expressing at least one heterologous nucleic acid molecule encoding for a polypeptide with the cyclase activity.

A preferred embodiment of the process according to the invention comprises at least the following steps a), b) and d):
a) to isolate or to recombinantly generate a microorganism producing an enzyme with cyclase activity from a natural source,
b) to multiply this microorganism,
c) optionally to isolate the enzyme with cyclase activity from the microorganism or to prepare a protein fraction comprising this enzyme, and
d) to transfer the microorganism of step b) or the enzyme of step c) into a medium which comprises a substrate of the general formula (I).

In the process according to the invention, a substrate is brought into contact and/or incubated with the cyclase enzyme in a medium in such a way that the substrate is reacted in the presence of the enzyme. The medium is preferably an aqueous reaction medium.

The pH of the aqueous reaction medium in which the process according to the invention is carried out by preference is advantageously maintained between pH 4 and 12, preferably between pH 4.5 and 9, especially preferably between pH 5 and 8.

The aqueous reaction media are preferably buffered solutions which, as a rule, have a pH of preferably from 5 to 8. A buffer which may be used can be a citrate, phosphate, TRIS (tris(hydroxymethyl)aminomethane) or MES buffer (2-(N-morpholino)ethanesulfonic acid). The reaction medium may additionally also comprise further additives such as, for example, detergents (for example taurodeoxycholate).

The substrate is preferably introduced into the enzymatic environment at a concentration of 2-200 mM, especially preferably 5-25 mM, and can be resupplied continuously or batchwise.

As a rule, the enzymatic cyclization takes place at a reaction temperature below the deactivation temperature of the enzyme used and above −10° C. Preferably, the process according to the invention is carried out at a temperature of between 0° C. and 95° C., especially preferably at a temperature of between 15° C. and 60° C., in particular between 20 and 45° C., for example at about 25 to 30° C.

Especially preferred is a process according to the invention in which the reaction is carried out at a temperature in the range of from 20 to 40° C. and/or a pH in the range of from 4 to 8.

Besides these single-phase aqueous systems, in another variant of the invention, two-phase systems are also used. Here, as well as an aqueous phase, organic non-water-miscible reaction media are used as the second phase. As a result, the reaction products accumulate in the organic phase. After the reaction, the product in the organic phase can readily be separated from the aqueous phase that comprises the biocatalyst.

The reaction product can be extracted using organic solvents and optionally distilled for purification.

Examples of suitable organic solvents are aliphatic hydrocarbons, preferably having 5 to 8 carbon atoms, such as pentane, cyclopentane, hexane, cyclohexane, heptane, octane or cyclooctane, halogenated aliphatic hydrocarbons, preferably having one or two carbon atoms, such as dichloromethane, chloroform, carbon tetrachloride, dichloroethane or tetrachloroethane, aromatic hydrocarbons, such as benzene, toluene, the xylenes, chlorobenzene or dichlorobenzene, aliphatic acyclic and cyclic ethers or alcohols, preferably having 4 to 8 carbon atoms, such as ethanol, isopropanol, diethyl ether, methyl tert-butyl ether, ethyl tert-butyl ether, dipropyl ether, diisopropyl ether, dibutyl ether, tetrahydrofuran or esters such as ethyl acetate or n-butyl acetate or ketones such as methyl isobutyl ketone or dioxane, or mixtures of these. The abovementioned heptane, methyl tert-butyl ether, diisopropyl ether, tetrahydrofuran, ethyl acetate are especially preferably used.

The cyclases used in accordance with the invention can be used in the process according to the invention as free or immobilized enzyme, as already described above.

For the process according to the invention, it is possible to use quiescent or growing, free or immobilized cells which comprise nucleic acids, nucleic acid constructs or vectors which code for the cyclase, Disrupted cells, such as cell lysates or cell homogenates, may also be used. Disrupted cells are understood as meaning, for example, cells which have been permeabilized by a treatment for example with solvents, or cells that have been disrupted by enzymatic treatment, by mechanical treatment (for example French press or ultrasound) or by some other method. The crude extracts thus obtained are advantageously suitable for the process according to the invention. Purified or partially purified enzymes may also be used for the process.

If free organisms or enzymes are used for the process according to the invention, they are expediently separated prior to the extraction, for example by filtration or centrifugation.

The process according to the invention can be operated batchwise, semibatchwise or continuously.

In an especially preferred embodiment of the process, the enzyme with cyclase activity is selected from among enzymes which comprise an amino acid sequence as shown in SEQ ID No. 2 or a sequence derived therefrom, in which up to 25%, preferably up to 20%, especially preferably up to 15%, in particular up to 10, 9, 8, 7, 6, 5, 4, 3, 2, 1% of the amino acid residues have been modified by a deletion, a substitution, an insertion or a combination of deletion, substitution and insertion. Here, these polypeptide sequences, which are modified in respect of SEQ ID No. 2, can still retain at least 50%, preferably 65%, especially preferably 80%, in particular more than 90%, of the enzymatic activity of SEQ ID No. 2. In this context, enzymatic activity of SEQ ID No. 2 is to be understood as the ability of biocatalytically cyclizing a compound of the general formula (I) to give the corresponding compound of the formula (II).

Experimental part

Unless specific information has been given in the examples which follow, the general information hereinbelow applies.

A. General information

All materials and microorganisms employed are commercially available products.

Unless otherwise specified, recombinant proteins are cloned and expressed by standard methods, such as, for example, as described by Sambrook, J., Fritsch, E. F. and Maniatis, T., Molecular cloning: A Laboratory Manual, $2^{nd}$ Edition, Cold Spring Harbor Laboratory, Cold Spring Harbor Laboratory Press, Cold Spring Harbor, N.Y., 1989.

a) Bacterial strains, plasmids and growth conditions

Inoculated from a suitable 2-ml preculture, E. coli LU15568 was grown in 20 ml Lytic Broth-Amp/Spec/Cm (100 µg/l ampicillin; 100 µg/l spectinomycin; 20 µg/l chloramphenicol), in 100-ml Erlenmeyer flasks (baffled) in the presence of 0.1 mM IPTG, 0.5 g/l rhamnose for 16 h at 37° C., and centrifuged for 10 min at 5000*g.

b) Cyclization Assay with Geranyllinalool (Standard Conditions)

Recombinant E. coli cells were suspended in 20 mM Tris-HCl pH 8.0 (3 ml per g moist cells). The cyclization mixture comprised 250 µl cell suspension, 50 µl 1 M citrate buffer (pH 4.5), 20 mM (final concentration) substrate and water to 500 µl. When squalene was cyclized, 1% (v/v) Triton-X100 was added. For the cyclization reaction, E. coli cells (6 g moist cells) were suspended in solubilization buffer (50 mM phosphate, 10 mM $MgCl_2$ (pH 6.5; total volume: 25 ml). The cells were disrupted at 1500 bar using a Manton-Gaulin homogenizer. Insoluble cell debris was removed by centrifugation (15 min at 4° C. and 7150*g).

For the reaction of geranyllinalool, 1.2 ml $KP_i$ buffer (50 mM potassium phosphate, pH 6.5; 10 mM $MgCl_2$) were mixed with 1 ml crude enzyme extract (protein content 39.3 mg/ml in 50 mM $KP_i$ buffer) and 22 µl geranyllinalool (from Sigma-Aldrich-Fluka; Order No. 48809) and incubated for three or twenty hours at 37° C. and 300 rpm in a 10 ml screw-top jar equipped with magnetic stirrer.

At the end of the incubation period, the samples were extracted with 5 ml n-heptane/1-propanol (3:2) and analyzed by GC. Controls were carried out with E. coli cells, which harboured an empty vector, and with heat-inactivated SHC-expressing cells.

c) Gas chromatography

Apparatus: Agilent 6890 series

Column: OPTIMA-1 TG ID: 0.32 mm, length: 10 m (Macherey-Nagel, Duren, Germany)

Flow rate: 1.0/min at 5.1 psi (and 80° C.)

Split: 1:50, split flow: 50 ml/min,

Carrier: nitrogen

Injector: split/splitless liner (Restec GmbH, Bad Homburg, Germany; Siltec-deactivated, 4*6.3*78.5 mm, glass wool) injector temperature 280° C.

Injection volume: 1 µl

Detector: FID with 300 ml/min air, 30 ml/min hydrogen and 30 ml/min nitrogen Detector temperature: 320° C.

Temperature program:
  Start: 100° C.
  Holding time 1: 0 min
  T ramp 1: 5° C./min
  T end 1: 200° C.
  Holding time 2: 5 min
  T ramp 2: 30° C./min
  T end 2: 320° C.
  Holding time 3: 20 min
  Total time: 49.0 min Data analysis: Empower-3 software Service Release 1 (Waters GmbH, Eschborn, Germany)

Retention time geranyllinalool: 14.4 min

B. EXAMPLES

Example 1

Cyclization of geranyllinalool by Zmo-SHC (SEQ ID No. 2)

a) Procedure:

Recombinant Zmo-SHC was generated as described by growing and disrupting LU 15568 (cf. PCT/EP2010/057696 (WO2010139719 A2)). To check this enzyme preparation, the activity was redetermined using homofarnesol as the reference substrate. The activity obtained (conversion rate 63% in 3 hours with 39 mg total protein) is within the scope of the results obtained to date under these conditions.

The reaction of geranyllinalool was carried out as described above under standard conditions.

At the end of the incubation period, the samples were extracted with 5 ml n-heptane/1-propanol (3:2) and analyzed by GC.

Reaction Equation:

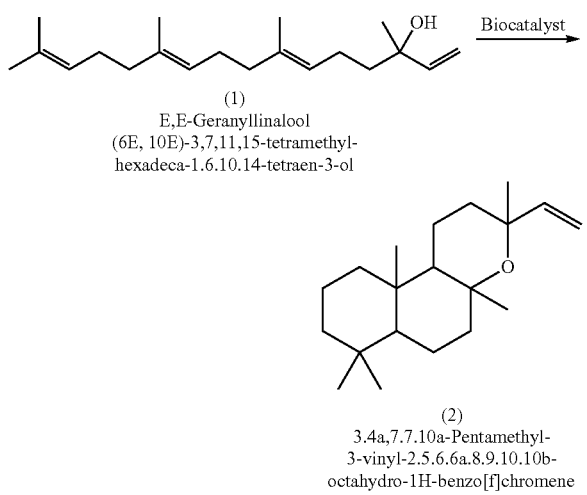

(1) E,E-Geranyllinalool
(6E, 10E)-3,7,11,15-tetramethyl-hexadeca-1.6.10.14-tetraen-3-ol (2) 3.4a,7.7.10a-Pentamethyl-3-vinyl-2.5.6.6a.8.9.10.10b-octahydro-1H-benzo[f]chromene b) Result After 20 hours, two enzyme-dependent peaks were found (retention time 13.3 and 13.7 min, respectively). The conversion rate based on the geranyllinalool employed is approximately 11%. By GC-MS analysis and interpreting the mass spectra, two structural isomers of the benzochromene derivative 2 were assigned to the two peaks.

The differences between the two peaks at 13.3 and 13.7 min, respectively, could not be elucidated by MS. For example, it is possible that they are stereoisomers of compound 2.

These peaks could not be detected in a negative control which had been incubated without enzyme addition.

This result demonstrates that the Zmo-SHC is also capable of cyclizing geranyllinalool (1). However, at least two isomers seem to occur in the reaction.

c) Summary:

It was possible for the first time to demonstrate the cyclization of geranyllinalool to a tricyclic vinylbenzochromene derivative by the recombinant squalene-hopene cyclase from *Zymomonas mobilis*.

Sequences:

SEQ ID No. 1: Nucleic acid sequence of Zmo-SHC
SEQ ID No. 2: Amino acid sequences of Zmo-SHC Reference is expressly made to the disclosure of the publications cited herein.

---

We claim:

1. A process for the biocatalytic cyclization of a compound of the formula (I)

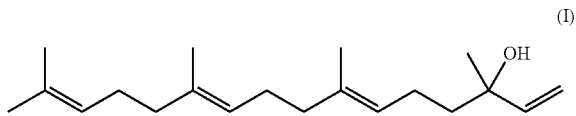 [SMILES: C=CC(C)(O)CC/C=C(\C)CC/C=C(\C)CCC=C(C)C]

(I)

in the presence of a cyclase which has the amino acid sequence as shown in SEQ ID No. 2 or which has at least 95% sequence identity to SEQ ID No. 2; wherein the compound of the formula (I) is reacted to give the compound of the formula (II)

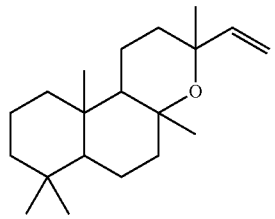

(II)

2. The process according to claim 1, wherein the cyclase is present in crude, purified, dissolved, dispersed or immobilized form, or in the presence of cyclase-displaying cells of a microorganism.

3. The process according to claim 1 in the presence of a recombinant microorganism which includes a nucleotide sequence which codes for the cyclase.

4. The process according to claim 3, wherein the nucleotide sequence is part of an expression cassette and, therein, is under the control of at least one regulatory sequence.

5. The process according to claim 4, wherein the expression cassette is part of an expression vector.

6. The process according to claim 5, wherein the expression vector is selected from among plasmids.

7. The process according to claim 2, wherein the microorganism is selected from among bacteria, fungi and yeasts.

8. The process according to claim 7, wherein the microorganism is *E. coli*.

9. The process according to claim 2 in the presence of a recombinant microorganism which includes a nucleotide sequence which codes for the cyclase.

10. The process according to claim 9, wherein the nucleotide sequence is part of an expression cassette and, therein, is under the control of at least one regulatory sequence.

11. The process according to claim 10, wherein the expression cassette is part of an expression vector.

12. The process according to claim 11, wherein the expression vector is selected from among plasmids.

13. The process according to claim 9, wherein the microorganism is selected from among bacteria, fungi and yeasts.

14. The process according to claim 13, wherein the microorganism is *E. coli*.

15. The process according to claim 3, wherein the microorganism is selected from among bacteria, fungi and yeasts.

16. The process according to claim 15, wherein the microorganism is *E. coli*.

* * * * *

SEQUENCE LISTING

```
<160> NUMBER OF SEQ ID NOS: 2

<210> SEQ ID NO 1
<211> LENGTH: 2178
<212> TYPE: DNA
<213> ORGANISM: Zymomonas mobilis
<220> FEATURE:
<221> NAME/KEY: CDS
<222> LOCATION: (1)..(2178)

<400> SEQUENCE: 1 atg ggt att gac aga atg aat agc tta agt cgc ttg tta atg aag aag       48
Met Gly Ile Asp Arg Met Asn Ser Leu Ser Arg Leu Leu Met Lys Lys
1               5                   10                  15 att ttc ggg gct gaa aaa acc tcg tat aaa ccg gct tcc gat acc ata       96
Ile Phe Gly Ala Glu Lys Thr Ser Tyr Lys Pro Ala Ser Asp Thr Ile
            20                  25                  30 atc gga acg gat acc ctg aaa aga ccg aac cgg cgg cct gaa ccg acg      144
Ile Gly Thr Asp Thr Leu Lys Arg Pro Asn Arg Arg Pro Glu Pro Thr
        35                  40                  45 gca aaa gtc gac aaa acg ata ttc aag act atg ggg aat agt ctg aat      192
Ala Lys Val Asp Lys Thr Ile Phe Lys Thr Met Gly Asn Ser Leu Asn
    50                  55                  60 aat acc ctt gtt tca gcc tgt gac tgg ttg atc gga caa caa aag ccc      240
Asn Thr Leu Val Ser Ala Cys Asp Trp Leu Ile Gly Gln Gln Lys Pro
65                  70                  75                  80 gat ggt cat tgg gtc ggt gcc gtg gaa tcc aat gct tcg atg gaa gca      288
Asp Gly His Trp Val Gly Ala Val Glu Ser Asn Ala Ser Met Glu Ala
                85                  90                  95 gaa tgg tgt ctg gcc ttg tgg ttt ttg ggt ctg gaa gat cat ccg ctt      336
Glu Trp Cys Leu Ala Leu Trp Phe Leu Gly Leu Glu Asp His Pro Leu
            100                 105                 110 cgt cca aga ttg ggc aat gct ctt ttg gaa atg cag cgg gaa gat ggc      384
Arg Pro Arg Leu Gly Asn Ala Leu Leu Glu Met Gln Arg Glu Asp Gly
```

```
                115                  120                  125
tct tgg gga gtc tat ttc ggc gct gga aat ggc gat atc aat gcc acg        432
Ser Trp Gly Val Tyr Phe Gly Ala Gly Asn Gly Asp Ile Asn Ala Thr
    130                  135                  140 gtt gaa gcc tat gcg gcc ttg cgg tct ttg ggg tat tct gcc gat aat        480
Val Glu Ala Tyr Ala Ala Leu Arg Ser Leu Gly Tyr Ser Ala Asp Asn
145                  150                  155                  160 cct gtt ttg aaa aaa gcg gca gca tgg att gct gaa aaa ggc gga tta        528
Pro Val Leu Lys Lys Ala Ala Ala Trp Ile Ala Glu Lys Gly Gly Leu
                165                  170                  175 aaa aat atc cgt gtc ttt acc cgt tat tgg ctg gcg ttg atc ggg gaa        576
Lys Asn Ile Arg Val Phe Thr Arg Tyr Trp Leu Ala Leu Ile Gly Glu
    180                  185                  190 tgg cct tgg gaa aag acc cct aac ctt ccc cct gaa att atc tgg ttc        624
Trp Pro Trp Glu Lys Thr Pro Asn Leu Pro Pro Glu Ile Ile Trp Phe
        195                  200                  205 cct gat aat ttt gtc ttt tcg att tat aat ttt gcc caa tgg gcg cgg        672
Pro Asp Asn Phe Val Phe Ser Ile Tyr Asn Phe Ala Gln Trp Ala Arg
    210                  215                  220 gca acc atg gtg ccg att gct att ctg tcc gcg aga cga cca agc cgc        720
Ala Thr Met Val Pro Ile Ala Ile Leu Ser Ala Arg Arg Pro Ser Arg
225                  230                  235                  240 ccg ctg cgc cct caa gac cga ttg gat gaa ctg ttt cca gaa ggc cgc        768
Pro Leu Arg Pro Gln Asp Arg Leu Asp Glu Leu Phe Pro Glu Gly Arg
                245                  250                  255 gct cgc ttt gat tat gaa ttg ccg aaa aaa gaa ggc atc gat ctt tgg        816
Ala Arg Phe Asp Tyr Glu Leu Pro Lys Lys Glu Gly Ile Asp Leu Trp
    260                  265                  270 tcg caa ttt ttc cga acc act gac cgt gga tta cat tgg gtt cag tcc        864
Ser Gln Phe Phe Arg Thr Thr Asp Arg Gly Leu His Trp Val Gln Ser
        275                  280                  285 aat ctg tta aag cgc aat agc ttg cgt gaa gcc gct atc cgt cat gtt        912
Asn Leu Leu Lys Arg Asn Ser Leu Arg Glu Ala Ala Ile Arg His Val
    290                  295                  300 ttg gaa tgg att atc cgg cat cag gat gcc gat ggc ggt tgg ggt gga        960
Leu Glu Trp Ile Ile Arg His Gln Asp Ala Asp Gly Gly Trp Gly Gly
305                  310                  315                  320 att cag cca cct tgg gtc tat ggt ttg atg gcg tta cat ggt gaa ggc       1008
Ile Gln Pro Pro Trp Val Tyr Gly Leu Met Ala Leu His Gly Glu Gly
                325                  330                  335 tat cag ctt tat cat ccg gtg atg gcc aag gct ttg tcg gct ttg gat       1056
Tyr Gln Leu Tyr His Pro Val Met Ala Lys Ala Leu Ser Ala Leu Asp
    340                  345                  350 gat ccc ggt tgg cga cat gac aga ggc gag tct tct tgg ata cag gcc       1104
Asp Pro Gly Trp Arg His Asp Arg Gly Glu Ser Ser Trp Ile Gln Ala
        355                  360                  365 acc aat agt ccg gta tgg gat aca atg ttg gcc ttg atg gcg tta aaa       1152
Thr Asn Ser Pro Val Trp Asp Thr Met Leu Ala Leu Met Ala Leu Lys
    370                  375                  380 gac gcc aag gcc gag gat cgt ttt acg ccg gaa atg gat aag gcc gcc       1200
Asp Ala Lys Ala Glu Asp Arg Phe Thr Pro Glu Met Asp Lys Ala Ala
385                  390                  395                  400 gat tgg ctt ttg gct cga cag gtc aaa gtc aaa ggc gat tgg tca atc       1248
Asp Trp Leu Leu Ala Arg Gln Val Lys Val Lys Gly Asp Trp Ser Ile
                405                  410                  415 aaa ctg ccc gat gtt gaa ccc ggt gga tgg gca ttt gaa tat gcc aat       1296
Lys Leu Pro Asp Val Glu Pro Gly Gly Trp Ala Phe Glu Tyr Ala Asn
    420                  425                  430 gat cgc tat ccc gat acc gat gat acc gcc gtc gct ttg atc gcc ctt       1344
```

```
                Asp Arg Tyr Pro Asp Thr Asp Asp Thr Ala Val Ala Leu Ile Ala Leu
                            435                 440                 445 tcc tct tat cgt gat aag gag gag tgg caa aag aaa ggc gtt gag gac          1392
Ser Ser Tyr Arg Asp Lys Glu Glu Trp Gln Lys Lys Gly Val Glu Asp
450                 455                 460 gcc att acc cgt ggg gtt aat tgg ttg atc gcc atg caa agc gaa tgt          1440
Ala Ile Thr Arg Gly Val Asn Trp Leu Ile Ala Met Gln Ser Glu Cys
465                 470                 475                 480 ggc ggt tgg gga gcc ttt gat aag gat aat aac aga agt atc ctt tcc          1488
Gly Gly Trp Gly Ala Phe Asp Lys Asp Asn Asn Arg Ser Ile Leu Ser
                485                 490                 495 aaa att cct ttt tgt gat ttc gga gaa tct att gat ccg cct tca gtc          1536
Lys Ile Pro Phe Cys Asp Phe Gly Glu Ser Ile Asp Pro Pro Ser Val
            500                 505                 510 gat gta acg gcg cat gtt tta gag gcc ttt ggc acc ttg gga ctg tcc          1584
Asp Val Thr Ala His Val Leu Glu Ala Phe Gly Thr Leu Gly Leu Ser
        515                 520                 525 cgc gat atg ccg gtc atc caa aaa gcg atc gac tat gtc cgt tcc gaa          1632
Arg Asp Met Pro Val Ile Gln Lys Ala Ile Asp Tyr Val Arg Ser Glu
530                 535                 540 cag gaa gcc gaa ggc gcg tgg ttt ggt cgt tgg ggc gtt aat tat atc          1680
Gln Glu Ala Glu Gly Ala Trp Phe Gly Arg Trp Gly Val Asn Tyr Ile
545                 550                 555                 560 tat ggc acc ggt gcg gtt ctg cct gct ttg gcg gcg atc ggt gaa gat          1728
Tyr Gly Thr Gly Ala Val Leu Pro Ala Leu Ala Ala Ile Gly Glu Asp
                565                 570                 575 atg acc cag cct tac atc acc aag gct tgc gat tgg ctg gtc gca cat          1776
Met Thr Gln Pro Tyr Ile Thr Lys Ala Cys Asp Trp Leu Val Ala His
            580                 585                 590 cag cag gaa gac ggc ggt tgg ggc gaa agc tgc tct tcc tat atg gag          1824
Gln Gln Glu Asp Gly Gly Trp Gly Glu Ser Cys Ser Ser Tyr Met Glu
        595                 600                 605 att gat tcc att ggg aag ggc cca acc acg ccg tcc cag act gct tgg          1872
Ile Asp Ser Ile Gly Lys Gly Pro Thr Thr Pro Ser Gln Thr Ala Trp
610                 615                 620 gct ttg atg ggg ttg atc gcg gcc aat cgt ccc gaa gat tat gaa gcc          1920
Ala Leu Met Gly Leu Ile Ala Ala Asn Arg Pro Glu Asp Tyr Glu Ala
625                 630                 635                 640 att gcc aag gga tgc cat tat ctg att gat cgc caa gag cag gat ggt          1968
Ile Ala Lys Gly Cys His Tyr Leu Ile Asp Arg Gln Glu Gln Asp Gly
                645                 650                 655 agc tgg aaa gaa gaa gaa ttc acc ggc acc gga ttc ccc ggt tat ggc          2016
Ser Trp Lys Glu Glu Glu Phe Thr Gly Thr Gly Phe Pro Gly Tyr Gly
            660                 665                 670 gtg ggt cag acg atc aag ttg gat gat ccg gct tta tcg aaa cga ttg          2064
Val Gly Gln Thr Ile Lys Leu Asp Asp Pro Ala Leu Ser Lys Arg Leu
        675                 680                 685 ctt caa ggc gct gaa ctg tca cgg gcg ttt atg ctg cgt tat gat ttt          2112
Leu Gln Gly Ala Glu Leu Ser Arg Ala Phe Met Leu Arg Tyr Asp Phe
    690                 695                 700 tat cgg caa ttc ttc ccg att atg gcg tta agt cgg gca gag aga ctg          2160
Tyr Arg Gln Phe Phe Pro Ile Met Ala Leu Ser Arg Ala Glu Arg Leu
705                 710                 715                 720 att gat ttg aat aat tga                                                   2178
Ile Asp Leu Asn Asn
                725

<210> SEQ ID NO 2
<211> LENGTH: 725
<212> TYPE: PRT
```

<213> ORGANISM: Zymomonas mobilis

<400> SEQUENCE: 2

```
Met Gly Ile Asp Arg Met Asn Ser Leu Ser Arg Leu Leu Met Lys Lys
1               5                   10                  15

Ile Phe Gly Ala Glu Lys Thr Ser Tyr Lys Pro Ala Ser Asp Thr Ile
            20                  25                  30

Ile Gly Thr Asp Thr Leu Lys Arg Pro Asn Arg Arg Pro Glu Pro Thr
        35                  40                  45

Ala Lys Val Asp Lys Thr Ile Phe Lys Thr Met Gly Asn Ser Leu Asn
    50                  55                  60

Asn Thr Leu Val Ser Ala Cys Asp Trp Leu Ile Gly Gln Gln Lys Pro
65                  70                  75                  80

Asp Gly His Trp Val Gly Ala Val Glu Ser Asn Ala Ser Met Glu Ala
                85                  90                  95

Glu Trp Cys Leu Ala Leu Trp Phe Leu Gly Leu Glu Asp His Pro Leu
            100                 105                 110

Arg Pro Arg Leu Gly Asn Ala Leu Leu Glu Met Gln Arg Glu Asp Gly
        115                 120                 125

Ser Trp Gly Val Tyr Phe Gly Ala Gly Asn Gly Asp Ile Asn Ala Thr
    130                 135                 140

Val Glu Ala Tyr Ala Ala Leu Arg Ser Leu Gly Tyr Ser Ala Asp Asn
145                 150                 155                 160

Pro Val Leu Lys Lys Ala Ala Trp Ile Ala Glu Lys Gly Gly Leu
                165                 170                 175

Lys Asn Ile Arg Val Phe Thr Arg Tyr Trp Leu Ala Leu Ile Gly Glu
            180                 185                 190

Trp Pro Trp Glu Lys Thr Pro Asn Leu Pro Pro Glu Ile Ile Trp Phe
        195                 200                 205

Pro Asp Asn Phe Val Phe Ser Ile Tyr Asn Phe Ala Gln Trp Ala Arg
    210                 215                 220

Ala Thr Met Val Pro Ile Ala Ile Leu Ser Ala Arg Arg Pro Ser Arg
225                 230                 235                 240

Pro Leu Arg Pro Gln Asp Arg Leu Asp Glu Leu Phe Pro Glu Gly Arg
                245                 250                 255

Ala Arg Phe Asp Tyr Glu Leu Pro Lys Lys Glu Gly Ile Asp Leu Trp
            260                 265                 270

Ser Gln Phe Phe Arg Thr Thr Asp Arg Gly Leu His Trp Val Gln Ser
        275                 280                 285

Asn Leu Leu Lys Arg Asn Ser Leu Arg Glu Ala Ala Ile Arg His Val
    290                 295                 300

Leu Glu Trp Ile Ile Arg His Gln Asp Ala Asp Gly Gly Trp Gly Gly
305                 310                 315                 320

Ile Gln Pro Pro Trp Val Tyr Gly Leu Met Ala Leu His Gly Glu Gly
                325                 330                 335

Tyr Gln Leu Tyr His Pro Val Met Ala Lys Ala Leu Ser Ala Leu Asp
            340                 345                 350
```

-continued

```
Asp Pro Gly Trp Arg His Asp Arg Gly Glu Ser Ser Trp Ile Gln Ala
        355                 360                 365
Thr Asn Ser Pro Val Trp Asp Thr Met Leu Ala Leu Met Ala Leu Lys
370                 375                 380
Asp Ala Lys Ala Glu Asp Arg Phe Thr Pro Glu Met Asp Lys Ala Ala
385                 390                 395                 400
Asp Trp Leu Leu Ala Arg Gln Val Lys Val Lys Gly Asp Trp Ser Ile
                405                 410                 415
Lys Leu Pro Asp Val Glu Pro Gly Trp Ala Phe Glu Tyr Ala Asn
            420                 425                 430
Asp Arg Tyr Pro Asp Thr Asp Thr Ala Val Ala Leu Ile Ala Leu
            435                 440                 445
Ser Ser Tyr Arg Asp Lys Glu Glu Trp Gln Lys Lys Gly Val Glu Asp
    450                 455                 460
Ala Ile Thr Arg Gly Val Asn Trp Leu Ile Ala Met Gln Ser Glu Cys
465                 470                 475                 480
Gly Gly Trp Gly Ala Phe Asp Lys Asp Asn Asn Arg Ser Ile Leu Ser
                485                 490                 495
Lys Ile Pro Phe Cys Asp Phe Gly Glu Ser Ile Asp Pro Pro Ser Val
            500                 505                 510
Asp Val Thr Ala His Val Leu Glu Ala Phe Gly Thr Leu Gly Leu Ser
            515                 520                 525
Arg Asp Met Pro Val Ile Gln Lys Ala Ile Asp Tyr Val Arg Ser Glu
    530                 535                 540
Gln Glu Ala Glu Gly Ala Trp Phe Gly Arg Trp Gly Val Asn Tyr Ile
545                 550                 555                 560
Tyr Gly Thr Gly Ala Val Leu Pro Ala Leu Ala Ala Ile Gly Glu Asp
                565                 570                 575
Met Thr Gln Pro Tyr Ile Thr Lys Ala Cys Asp Trp Leu Val Ala His
            580                 585                 590
Gln Gln Glu Asp Gly Gly Trp Gly Glu Ser Cys Ser Ser Tyr Met Glu
    595                 600                 605
Ile Asp Ser Ile Gly Lys Gly Pro Thr Thr Pro Ser Gln Thr Ala Trp
610                 615                 620
Ala Leu Met Gly Leu Ile Ala Ala Asn Arg Pro Glu Asp Tyr Glu Ala
625                 630                 635                 640
Ile Ala Lys Gly Cys His Tyr Leu Ile Asp Arg Gln Glu Gln Asp Gly
                645                 650                 655
Ser Trp Lys Glu Glu Phe Thr Gly Thr Gly Phe Pro Gly Tyr Gly
            660                 665                 670
Val Gly Gln Thr Ile Lys Leu Asp Asp Pro Ala Leu Ser Lys Arg Leu
            675                 680                 685
Leu Gln Gly Ala Glu Leu Ser Arg Ala Phe Met Leu Arg Tyr Asp Phe
    690                 695                 700
Tyr Arg Gln Phe Phe Pro Ile Met Ala Leu Ser Arg Ala Glu Arg Leu
705                 710                 715                 720
Ile Asp Leu Asn Asn
            725
```